(12) United States Patent
Share

(10) Patent No.: US 10,584,188 B2
(45) Date of Patent: Mar. 10, 2020

(54) LED-CURABLE LOW MIGRATION PHOTOINITIATORS

(71) Applicant: IGM MALTA LIMITED, Gzira (MT)

(72) Inventor: Paul Share, Ann Arbor, MI (US)

(73) Assignee: IGM MALTA LIMITED, Gzira (MT)

( * ) Notice: Subject to any disclaimer, the term of this patent is extended or adjusted under 35 U.S.C. 154(b) by 0 days.

(21) Appl. No.: 16/378,782

(22) Filed: Apr. 9, 2019

(65) Prior Publication Data

US 2019/0233550 A1 Aug. 1, 2019

Related U.S. Application Data

(62) Division of application No. 15/541,115, filed as application No. PCT/US2016/012035 on Jan. 4, 2016, now Pat. No. 10,301,399.

(60) Provisional application No. 62/099,728, filed on Jan. 5, 2015.

(51) Int. Cl.

| | | |
|---|---|---|
| C08F 2/46 | (2006.01) | |
| C08F 2/50 | (2006.01) | |
| C08G 61/04 | (2006.01) | |
| C07D 295/15 | (2006.01) | |
| C09D 4/00 | (2006.01) | |
| C08F 20/18 | (2006.01) | |
| C08F 222/10 | (2006.01) | |

(52) U.S. Cl.
CPC .............. C08F 2/50 (2013.01); C07D 295/15 (2013.01); C09D 4/00 (2013.01); *C08F 20/18* (2013.01); *C08F 2222/1026* (2013.01)

(58) Field of Classification Search
None
See application file for complete search history.

(56) References Cited

U.S. PATENT DOCUMENTS

| | | | |
|---|---|---|---|
| 4,147,604 A | 4/1979 | Kuesters et al. | |
| 2005/0037277 A1 | 2/2005 | Herlihy et al. | |
| 2005/0261388 A1 | 11/2005 | Gould et al. | |
| 2007/0244210 A1* | 10/2007 | Herlihy .............. | C07D 295/112 522/26 |
| 2011/0063388 A1* | 3/2011 | Loccufier .............. | C07C 217/22 347/100 |
| 2015/0034886 A1 | 2/2015 | Lee et al. | |

FOREIGN PATENT DOCUMENTS

| | | |
|---|---|---|
| EP | 0 143 201 B1 | 8/1987 |
| EP | 0 554 005 A1 | 8/1993 |
| JP | 02-004745 B | 1/1990 |
| JP | 10-195026 A | 7/1998 |
| JP | 2007-534792 A | 11/2007 |
| JP | 2012-521453 A | 9/2012 |
| JP | 2013-025194 A | 2/2013 |
| JP | 2013-177516 A | 9/2013 |
| WO | WO-2013/176383 A1 | 11/2013 |
| WO | WO-2013/182533 A1 | 12/2013 |

OTHER PUBLICATIONS

Database WPI, Week 201313, Thomson Scientific, AN 2013-872665, xP002784658 (Feb. 2013).
Extended European Search Report in EP Application No. 16735253.3, dated Sep. 24, 2018 (8 pages).
Faghihi et al., "Novel thermally stable poly(amide-imide)s containing dibenzalacetone moiety in the main chain: Synthesis and characterization," M. Macromol. Res. (2010) 18: 421-428.
International Search Report & Written Opinion in International Application No. PCT/US2016/012035, dated Jun. 3, 2016 (13 pages).
Non-Final Office Action in U.S. Appl. No. 15/541,115, dated Aug. 23, 2018 (9 pages).
Notice of Allowance in U.S. Appl. No. 15/541,115, dated Jan. 10, 2019 (12 pages).
Notice of Reasons for Rejection in JP Application No. 2017-535803, dated Jul. 24, 2018. (English translation included—10 pages).
Onen et al., "Synthesis of a novel addition-fragmentation agent based on Michler's ketone and its use as photo-initiator for cationic polymerization," Polymer 42 (2001) 6681-6685.
Spange et al., "Solid-state Structures of N-Substituted Michler's Ketones and Their Relation to Solvatochromism," Eur. J. Org. Chem. (2002), 4159-4168.
Wang et al., "Novel polymerizable N-aromatic maleimides as free radical initiators for photopolymerization," Polym Int 55: 930-937 (2006).
Wen et al., "Polymeric Michler's Ketone Photoinitiator Containing Coinitiator Amine," Polymer Engineering and Science (2009) pp. 1608-1615.
Wen et al., "Polymeric Michler's ketone photoinitiators: The effect of chain flexibility," Progress in Organic Coatings 66 (2009) 65-72.

\* cited by examiner

*Primary Examiner* — Jessica Whiteley
(74) *Attorney, Agent, or Firm* — Foley & Lardner LLP

(57) ABSTRACT

A photoinitiator of Formula I includes a benzophenone moiety, a nitrogen-containing moiety (NCM) covalently bonded to the benzophenone moiety, and an unsaturated polymerizable moiety (PM) covalently bonded to the nitrogen-containing moiety. The unsaturated polymerizable moiety includes an acrylate group or a methacrylate group.

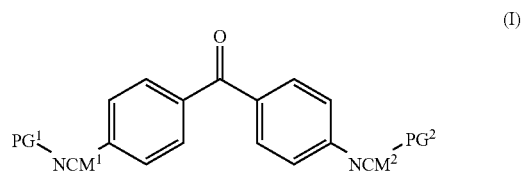

(I)

18 Claims, No Drawings

LED-CURABLE LOW MIGRATION PHOTOINITIATORS

CROSS-REFERENCE TO RELATED APPLICATIONS

This application is a divisional application of U.S. patent application Ser. No. 15/541,115, filed on Jun. 30, 2017, which is a U.S. National Phase Application under 35 U.S.C. § 371 of International Application No. PCT/US2016/012035, filed on Jan. 4, 2016, which in turn claims the benefit of U.S. Provisional Application No. 62/099,728, filed Jan. 5, 2015, the contents of each of which are incorporated herein by reference in their entirety.

FIELD

The present technology is generally related to photoinitiators for polymerizations. More specifically it is related to photoinitiators that may be bound to a resulting polymer upon photoinitiation by LED light sources.

BACKGROUND

The market for UV curable printing inks and coatings is changing from the use of mercury light sources to light emitting diode (LED) light sources. The current commercial photoinitiators used in these formulations are optimized for the short wavelength emissions from mercury lamps, and are very inefficient at the longer wavelengths associated with LED light sources. There are some photoinitiators such as isopropylthioxanthone (ITX) and Michler's ketone that are effective at longer wavelengths.

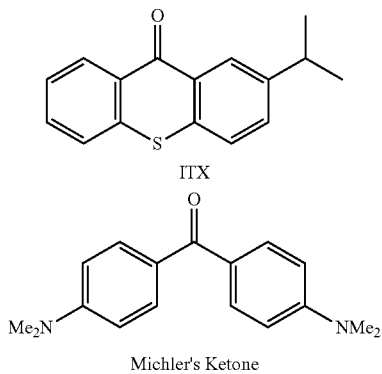

However, ITX and Michler's Ketone are low molecular weight materials that can migrate out of food and beverage packaging materials, which have prepared with these photoinitiators, and into the food and beverages. There are polymeric versions of ITX available, but these are less effective than ITX itself. There is therefore a need in the marketplace for a photoinitiator which functions well under LED illumination, and which does not migrate from products after curing.

SUMMARY

In one aspect, a photoinitiator is provided, which includes a benzophenone moiety, a nitrogen-containing moiety covalently bonded to the benzophenone moiety, and an unsaturated polymerizable moiety covalently bonded to the nitrogen-containing moiety.

In another aspect, a method of polymerization is provided, the method including mixing a photoinitiator with a polymerization composition to form a polymerizable mixture, and illuminating the polymerizable mixture with light from a light source, wherein the polymerization composition includes an acrylate, a methacrylate, or a styrenic monomer, and the photoinitiator includes a benzophenone moiety, a nitrogen-containing moiety covalently bonded to the benzophenone moiety, and an unsaturated polymerizable moiety covalently bonded to the nitrogen-containing moiety.

In yet another aspect, a method of curing a photocurable coating composition is provided, wherein the method includes illuminating the photocurable coating composition with light from a light emitting diode, wherein the photocurable coating composition includes an acrylate, a methacrylate, or a styrenic monomer; and a photoinitiator. The photoinitiator includes a benzophenone moiety, a nitrogen-containing moiety covalently bonded to the benzophenone moiety, and an unsaturated polymerizable moiety covalently bonded to the nitrogen-containing moiety.

In one aspect, a photocurable composition is provided, which includes an acrylate, a methacrylate, or a styrenic monomer and a photoinitiator, wherein the photoinitiator includes a benzophenone moiety, a nitrogen-containing moiety covalently bonded to the benzophenone moiety, and an unsaturated polymerizable moiety covalently bonded to the nitrogen-containing moiety.

In one aspect, provided is a compound represented by the following formula (II):

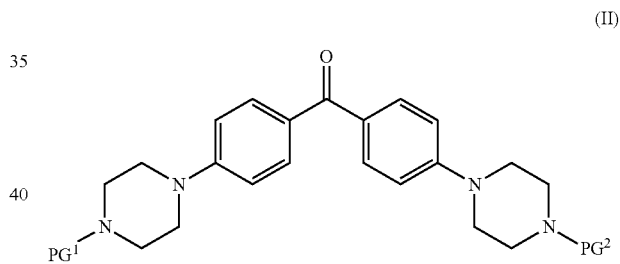

wherein: $PG^1$ and $PG^2$ are selected from the group consisting of:

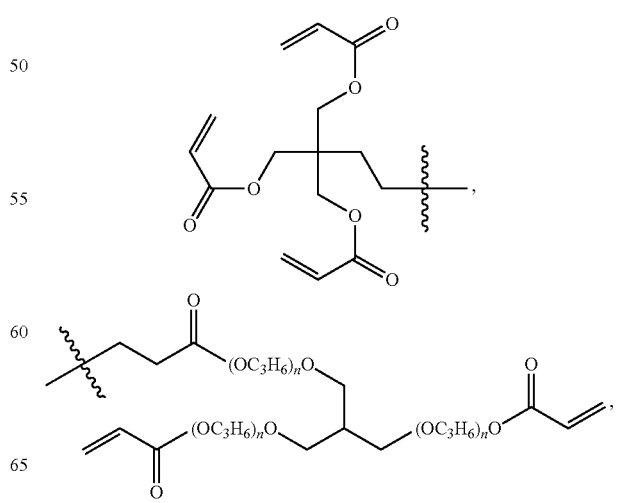

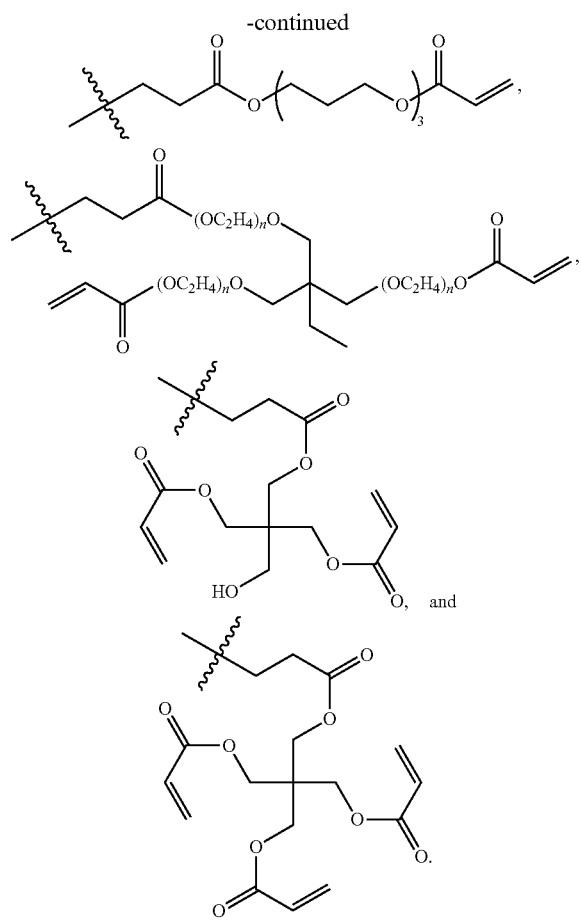

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and may be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to a group in which one or more bonds to a hydrogen atom contained therein is replaced by a bond to a non-hydrogen or non-carbon atom. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched alkyl groups having from 1 to 20 carbon atoms or, in some embodiments, from 1 to 12, 1 to 8, 1 to 6, or 1 to 4 carbon atoms. Alkyl groups further include cycloalkyl groups. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. Where the term haloalkyl is used, the alkyl group is substituted with one or more halogen atoms.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, CH=CH(CH$_3$), CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others. Representative substituted alkynyl groups may be mono-substituted or substituted more than once, such as, but not limited to, mono-, di- or tri-substituted with substituents such as those listed above.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

Heterocyclyl or heterocycle refers to both aromatic and nonaromatic ring compounds including monocyclic, bicyclic, and polycyclic ring compounds containing 3 or more ring members of which one or more is a heteroatom such as, but not limited to, N, O, and S. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridinyl, dihydropyridinyl, pyrimidinyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g., 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene oxide and tetrahydrothiophene 1,1-dioxide. Typical heterocyclyl groups contain 5 or 6 ring members. Thus, for example, heterocyclyl groups include morpholinyl, piperazinyl, piperidinyl, pyrrolidinyl, imidazolyl, pyrazolyl, 1,2,3-triazolyl, 1,2,4-triazolyl, tetrazolyl, thiophenyl, thiomorpholinyl, thiomorpholinyl in which the S atom of the thiomorpholinyl is bonded to one or more O atoms, pyrrolyl, pyridinyl homopiperazinyl, oxazolidin-2-onyl, pyrrolidin-2-onyl, oxazolyl, quinuclidinyl, thiazolyl, isoxazolyl, furanyl, and tetrahydrofuranyl. Heterocyclyl or heterocycles may be substituted.

As used herein, the term "acrylates" or "methacrylates" refers to acrylic or methacrylic acid, esters of acrylic or methacrylic acid, and salts, amides, and other suitable derivatives of acrylic or methacrylic acid, and mixtures thereof.

As used herein, the term "acrylic-containing group" or "methacrylate-containing group" refers to a compound that has a polymerizable acrylate or methacrylate group.

As used herein the term "solvent" refers to any inert fluid which does not react with the monomers or reactants during reaction such as polymerization.

The term "styrenic monomers" as used herein refers to aryl vinyl monomers such as styrene, substituted styrenes and ring-substituted styrenes. Exemplary styrenic monomers include styrene, α-methyl styrene, vinyl toluene, α-methylstyrene, o-methylstyrene, m-methylstyrene, p-methylstyrene, t-butyl styrene, vinyl pyridine, ring-α- or β-substituted bromostyrene, o-chlorostyrene, and p-chlorostyrene.

As used herein, the term epoxy-functional includes both epoxides and functional equivalents of such materials, such as oxazolines. Examples of epoxy-functional monomers include, but are not limited to, those containing 1,2-epoxy groups such as glycidyl acrylate and glycidyl methacrylate. Other suitable epoxy-functional monomers include allyl glycidyl ether, glycidyl ethacrylate, glycidyl itoconate, and other glycidyl(meth)acrylates Described herein are compounds that have a moiety that is a UV-active initiator covalently bonded to a monomeric moiety, such that upon activation by UV light the initiator is then tied into a resulting polymer. The compounds described are activatable under suitable light sources, e.g., LED (light emitting diode) light sources, thus providing for light-curable polymers and resins.

In one aspect, a LED-curable, low migration photoinitiator is provided. The photoinitiator includes a benzophenone moiety, a nitrogen-containing moiety covalently bonded to the benzophenone moiety, and an unsaturated polymerizable moiety covalently bonded to the nitrogen-containing moiety (NCM).

The unsaturated polymerizable moiety may include, an acrylate group or a methacrylate group. In some embodiments, the unsaturated polymerizable moiety includes an acrylate-containing group having two or more acrylate moieties, or a methacrylate-containing group having two or more methacrylate moieties. Suitable acrylate or methacrylate moieties include, but are not limited to, methyl acrylate, ethyl acrylate, n-propyl acrylate, isopropyl acrylate, n-butyl acrylate (BA), n-decyl acrylate, isobutyl acrylate, n-amyl acrylate, n-hexyl acrylate, isoamyl acrylate, 2-hydroxyethyl acrylate, 2-hydroxypropyl acrylate, N,N-dimethylaminoethyl acrylate, N,N-diethylaminoethyl acrylate, t-butylaminoethyl acrylate, 2-sulfoethyl acrylate, trifluoroethyl acrylate, glycidyl acrylate, benzyl acrylate, allyl acrylate, 2-n-butoxyethyl acrylate, 2-chloroethyl acrylate, sec-butyl-acrylate, tert-butyl acrylate, 2-ethylbutyl acrylate, cinnamyl acrylate, crotyl acrylate, cyclohexyl acrylate, cyclopentyl acrylate, 2-ethoxyethyl acrylate, furfuryl acrylate, hexafluoroisopropyl acrylate, methallyl acrylate, 3-methoxybutyl acrylate, 2-methoxybutyl acrylate, 2-nitro-2-methylpropyl acrylate, n-octylacrylate, 2-ethylhexyl acrylate, 2-phenoxyethyl acrylate, 2-phenylethyl acrylate, phenyl acrylate, propargyl acrylate, tetrahydrofurfuryl acrylate and tetrahydropyranyl acrylate, methyl methacrylate, ethyl methacrylate, n-propyl methacrylate, n-butyl methacrylate (BMA), isopropyl methacrylate, isobutyl methacrylate, n-amyl methacrylate, n-hexyl methacrylate, isoamyl methacrylate, 2-hydroxyethyl methacrylate, 2-hydroxypropyl methacrylate, N,N-dimethylaminoethyl methacrylate, N,N-diethylaminoethyl methacrylate, t-butylaminoethyl methacrylate, 2-sulfoethyl methacrylate, trifluoroethyl methacrylate, glycidyl methacrylate (GMA), benzyl methacrylate, allyl methacrylate, 2-n-butoxyethyl methacrylate, 2-chloroethyl methacrylate, sec-butyl-methacrylate, tert-butyl methacrylate, 2-ethylbutyl methacrylate, cinnamyl methacrylate, crotyl methacrylate, cyclohexyl methacrylate, cyclopentyl methacrylate, 2-ethoxyethyl methacrylate, furfuryl methacrylate, hexafluoroisopropyl methacrylate, methallyl methacrylate, 3-methoxybutyl methacrylate, 2-methoxybutyl methacrylate, 2-nitro-2-methylpropyl methacrylate, n-octylmethacrylate, 2-ethylhexyl methacrylate, 2-phenoxyethyl methacrylate, 2-phenylethyl methacrylate, phenyl methacrylate, propargyl methacrylate, tetrahydrofurfuryl methacrylate and tetrahydropyranyl methacrylate. Examples of other suitable acrylic and methacrylic moieties include, but are not limited to hydroxyalkyl acrylates and methacrylates, acrylic acid and its salts, acrylonitrile, acrylamide, methyl α-chloroacrylate, methyl 2-cyanoacrylate, N-ethylacrylamide, N,N-diethylacrylamide, acrolein, methacrylic acid and its salts, methacrylonitrile, methacrylamide, N-methylmethacrylamide, N-ethylmethacrylamide, N,N-diethylmethacrylamide, N,N-dimethylmethacrylamide, N-phenylmethacrylamide, methacrolein and acrylic or methacrylic acid derivatives containing cross-linkable functional groups, such as hydroxy, carboxyl, amino, isocyanate, glycidyl, epoxy, allyl, and the like.

Suitable polymerizable moieties may include, but are not limited to, trimethylolpropane triacrylate (TMPTA), propoxylated glycerol triacrylate (GPTA), pentaerythritol triaacrylate (PETA), pentaerythritol tetraacrylate (PETTA), ethoxylated trimethylolpropane triacrylate (EOTMPTA), 3-(acryloyloxy)propyl butyrate, 2-((butyryloxy)methyl)-2-(hydroxymethyl)propane-1,3-diyl diacrylate, 2-((acryloyloxy)methyl)-2-((butyryloxy)methyl)propane-1,3-diyl diacrylate, tris(2-hydroxyethyl) isocyanurate triacrylate, methyl methacrylate (MAA), tetrahydrofuryl methacrylate (THFMA), cyclohexyl methacrylate (CHMA), isobornyl methacrylate (IBMA), benzyl methacrylate (BMA), dicyclopentadienyloxyethyl methacrylate (DCPOEMA), tert-butyl methacrylate (tBMA), isobornyl acrylate (IBA), dihydrodicyclopentadienyl acrylate (DHDCPA), tripropylene glycol diacrylate (TPGDA), alkoxylated pentaerythritol tetraacrylate (PPTTA), propoxylated neopentyl glycol diacrylate (NPGPODA), hydroxyethyl methacrylate (HEMA), trimethylolpropane formal acrylate (CTFA), hexanediol diacrylate (HDDA), hydroxyethyl methacrylate (HEMA), hydroxypropyl methacrylate (HPMA), butyl-urethane-ethyl acrylate (BUEA), triethylene glycol dimethacrylate (TEGDMA), dipropylene glycol diacrylate (DPGDA), polyethylene glycol (600) diacrylate (PEG(600)DA), bisphenol A ethoxylated diacrylate (BPA8EPDA), pentaerythritol triacrylate (PETIA), ditrimethylolpropane tetra-acrylate (DiTMPTTA), and dipentaerythritol hexaacrylate (DPHA), phenoxy ethyleneglycol acrylate (AMP-10G), 2,2-bis[4-(acryloxypolyethoxy)phenyl]propane (A-BPE-10), and the like or derivatives thereof, or combinations thereof.

In some embodiments, the unsaturated polymerizable moiety is selected from the group consisting of trimethylolpropane triacrylate, propoxylated glyceryl triacrylate, tripropylene glycol diacrylate, pentaerythritol triacrylate, pentaerythritol tetraacrylate, and ethoxylated trimethylolpropane triacrylate.

The unsaturated polymerizable moiety is covalently bonded to both the benzophenone moiety and the nitrogen-containing moiety. Suitable nitrogen-containing moieties include, for example, nitrogen-containing heterocycles or hetereoaryls, and aliphatic amines. Representative examples of nitrogen-containing heterocycles include, but are not limited to, azepanyl, azetidinyl, aziridinyl, azocanyl, morpholinyl, piperazinyl, piperidinyl, pyrrolidinyl, pyrrolinyl, dihydrothiazolyl, imidazolyl, dihydropyridinyl, and thiomorpholinyl. Examples of aliphatic amines include primary and secondary amines.

In some embodiments, the nitrogen-containing moiety is an azetidinyl, pyrrolidinyl, piperazinyl, piperidinyl, azepanyl, azocanyl, or a group of formula —RNHR', where R is an alkylenyl group joining the nitrogen atom to the benzophenone, and R' is an alkyl group.

In some embodiments, R is an $C_1$-$C_{12}$ alkylenyl group. In some embodiments, R' is an $C_1$-$C_{12}$ alkyl group. In some embodiments, R is $C_1$-$C_6$ alkylenyl group. In some embodiments, R' is $C_1$-$C_6$ alkyl group. In some embodiments, R is methylene, ethylene, propylene, or butylene. In some embodiments, R' is methyl, ethyl, n-propyl, isopropyl, n-butyl, tert butyl, isobutyl, or sec-butyl.

In some embodiments, the nitrogen-containing moiety is a nitrogen-containing heterocycle. In some embodiments, the nitrogen-containing moiety is a piperazinyl based moiety.

In one aspect a photoinitiator is provided, which is represented by the formula (I):

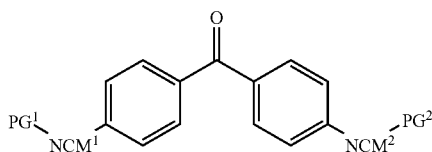

(I)

wherein:
NCM¹ is a first nitrogen-containing moiety where the nitrogen is covalently bonded to a first phenyl group of the benzophenone;
NCM² is a bond, H, or a second nitrogen-containing moiety where the nitrogen is covalently bonded to a second phenyl group of the benzophenone;
PG¹ is an acrylate-containing group or a methacrylate-containing group; and
PG² is absent, H, an acrylate-containing group or a methacrylate-containing group.

In some embodiments, $PG^1$ and $PG^2$ are an acrylate-containing group or a methacrylate-containing group. In some embodiments, PG1 and PG2 are individually an acrylate-containing group having two or more acrylate moieties, or a methacrylate-containing group having two or more methacrylate moieties. Suitable acrylate- or methacrylate-containing groups are as described herein. In some embodiments, the acrylate- or methacrylate-containing groups include an unsaturated polymerizable moiety selected from the group consisting of trimethylolpropane triacrylate, propoxylated glyceryl triacrylate, tripropylene glycol diacrylate, pentaerythritol triacrylate, pentaerythritol tetraacrylate, and ethoxylated trimethylolpropane triacrylate.

$NCM^1$ and $NCM^2$ each represent a nitrogen-containing moiety. Suitable nitrogen-containing moieties are as described herein. $NCM^1$ and $NCM^2$ may be the same or different nitrogen-containing moiety. In some embodiments, at least one of $NCM^1$ and $NCM^2$ is an azetidinyl, pyrrolidinyl, piperazinyl, piperidinyl, azepanyl, azocanyl, or a group of formula —RNR'H, where R is an alkylenyl group joining the nitrogen atom to the benzophenone, and R' is an alkyl group. In some embodiments, at least one of $NCM^1$ and $NCM^2$ is a piperazine-based moiety.

In one aspect a photoinitiator is provided, which is represented by formula (II):

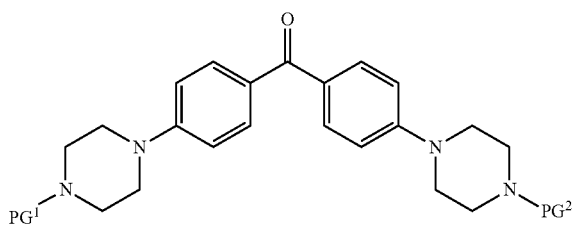

(II)

In some embodiments, for photoinitiators of formula (II), $PG^1$ and $PG^2$ are an acrylate-containing group or a methacrylate-containing group. In some embodiments, $PG^1$ and $PG^2$ are individually an acrylate-containing group having two or more acrylate moieties, or a methacrylate-containing group having two or more methacrylate moieties. Suitable acrylate- or methacrylate-containing groups are as described herein. In some embodiments, the acrylate- or methacrylate-containing groups include an unsaturated polymerizable moiety selected from the group consisting of trimethylolpropane triacrylate, propoxylated glyceryl triacrylate, tripropylene glycol diacrylate, pentaerythritol triacrylate, pentaerythritol tetraacrylate, and ethoxylated trimethylolpropane triacrylate.

In some embodiments, $PG^1$ and $PG^2$ are selected from the group consisting of:

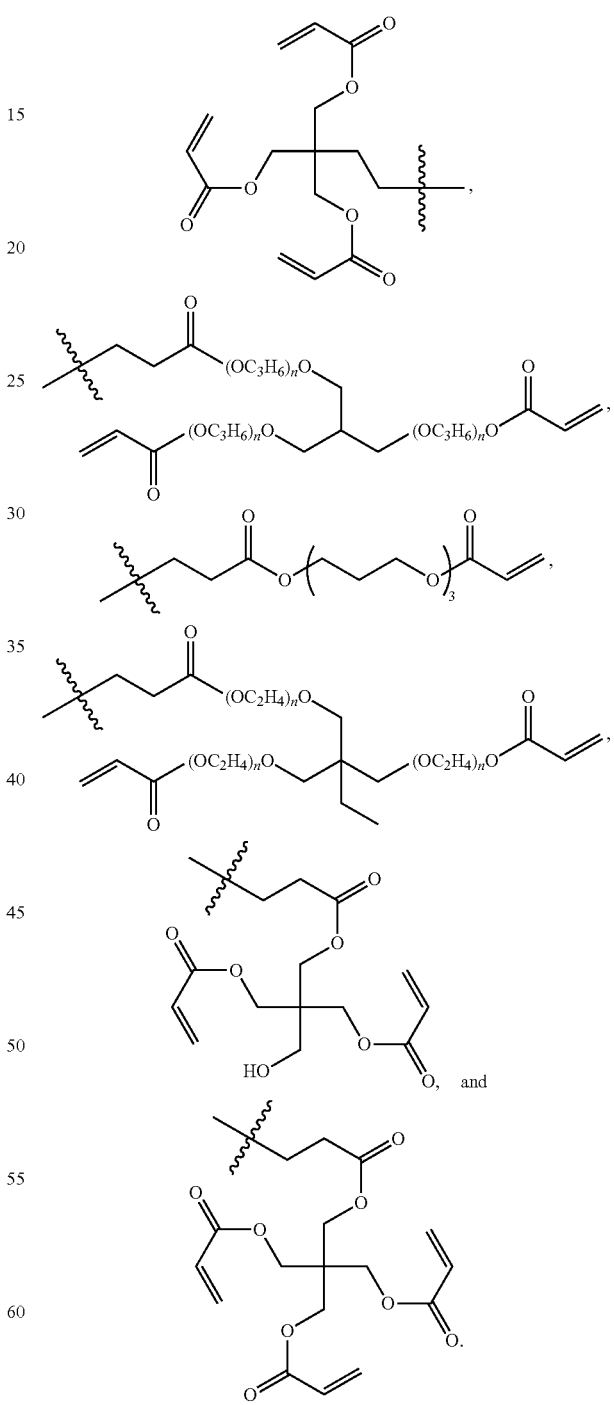

In some embodiments, a compound represented by the formula (II) is provided:

(II)

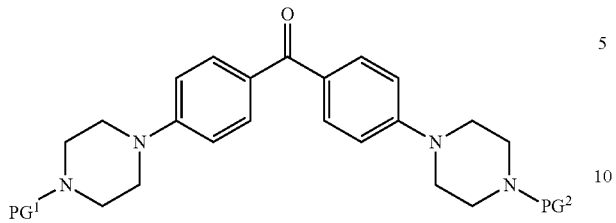

wherein: PG¹ and PG² are selected from the group consisting of:

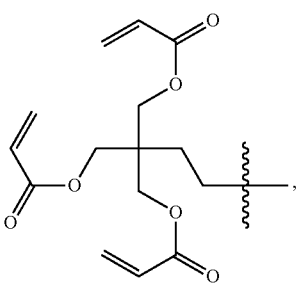

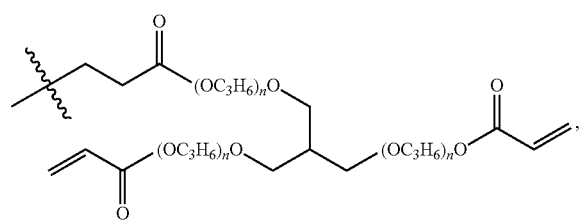

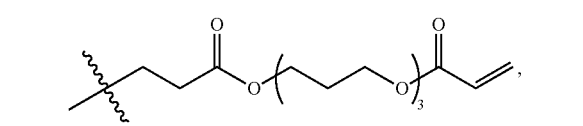

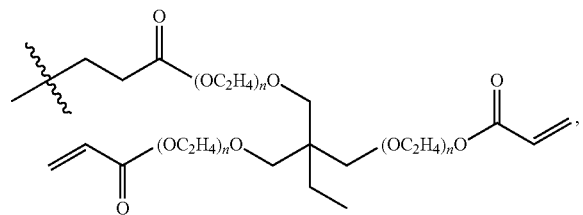

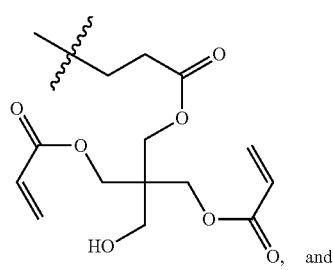, and

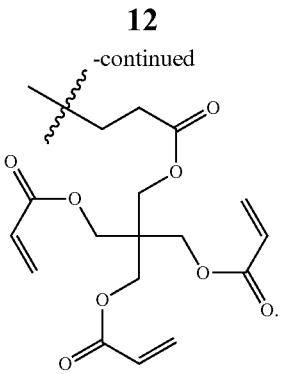

In some embodiments, PG¹ and PG² are:

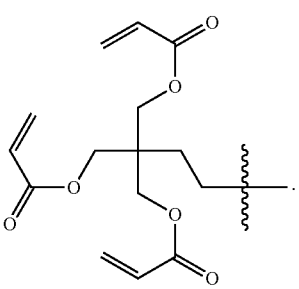

In one aspect, a reaction product of 4,4'-dihalobenzophenone, piperazine, and a multifunctional UV monomer is provided. Illustrative multifunctional UV monomers that may be used include, but are not limited to trimethylolpropane triacrylate (TMPTA), propoxylated glyceryl triacrylate (GPTA), tripropylene glycol diacrylate (TPGDA), pentaerythritol triacrylate (PETA), pentaerythritol tetraacrylate (PETTA), and ethoxylated trimethylolpropane triacrylate (EOTMPTA).

The linkage of the piperazine, or other nitrogen-containing moiety, to the benzophenone moiety provides at least three functional advantages. First, the piperazine is an electron donor to the benzophenone chromophore. This shifts the maximum absorption wavelength from 250 nm to a region from about 340 to 390 nm. This higher nanometer region is better-suited for LED-initiated chemistries. Second, the benzophenone is a Norrish type-2 initiator. The benzophenone reacts by abstracting a hydrogen from another molecule, typically a carbon which is alpha to a nitrogen. The third function is that the intermediate has two disubstituted nitrogens that may be used for additional chemical reactions.

In the photoinitiator, the free amine groups of the piperazines on the benzophenone are available for Michael addition reaction with multifunctional materials having more than one unsaturated site. Connecting a multifunctional material to the benzophenone-NCM provides for the photoinitiator itself to become part of the cross-linked polymer matrix that is formed, thus keeping the initiator sequestered within the product, and not available for ready extraction from the polymer matrix. For example, where the photoinitiator is used in applications such as a coating, packaging, or ink, migration of the photoinitiator from the coating, packaging, or ink is prevented, or at least minimized. The functionalization increases the molecular weight of the material, and increases the cross-linking in products formed therefrom.

In one aspect, polymers which includes the photoinitiators described herein, are provided. In one aspect, a polymer is provided, which includes a monomeric unit including the compound of formula (I). In another aspect, a polymer is provided, which includes a monomeric unit including the compound of formula (II). In some embodiments, the polymer may include mixtures of two or more monomers.

In one aspect, a method of polymerization is provided, wherein the method includes mixing a photoinitiator with a polymerization composition to form a polymerizable mixture and illuminating the polymerizable mixture with light from a light source.

The polymerization composition may include an acrylate, a methacrylate, or a styrenic monomer, as well as a mixture of any two or more thereof, and a hydroxylated acrylic or hydroxylated methacrylic monomer, allyl alcohol, or mixture of any two or more thereof. Illustrative (meth)acrylic monomers include, but are not limited to, (meth)acrylic acid, methyl (meth)acrylate, ethyl (meth)acrylate, n-propyl (meth)acrylate, n-butyl (meth)acrylate, isopropyl (meth) acrylate, isobutyl (meth)acrylate, isobornyl (meth)acrylate, cyclohexyl (meth)acrylate, and 2-ethylhexyl (meth)acrylate. Illustrative styrenic monomers include, but are not limited to, styrene and α-methylstyrene. Mixtures of any two more acrylic monomers, methacrylic monomers, or styrenic monomers may also be used. Necessary hydroxyl functionality is supplied by hydroxylated acrylic or hydroxylated methacrylic monomers, or even allyl alcohol. Examples of hydroxy-functional (meth)acrylates include, but are not limited to, 2-hydroxyethyl acrylate, 2-hydroxyethyl methacrylate, hydroxypropyl acrylate, hydroxypropyl methacrylate, and hydroxybutyl acrylate.

In some embodiments, the polymerization composition includes acrylic, methacrylic, or styrenic monomer selected from the group consisting of acrylic acid, methacrylic acid, methyl methacrylate, ethyl acrylate, ethyl methacrylate, n-propyl acrylate, n-propyl methacrylate, n-butyl acrylate, n-butyl methacrylate, isopropyl acrylate, isopropyl methacrylate, isobutyl acrylate, isobutyl methacrylate, n-amyl acrylate, n-amyl methacrylate, n-hexyl acrylate, n-hexyl methacrylate, isoamyl acrylate, isoamyl methacrylate, trifluoroethyl acrylate, trifluoroethyl methacrylate, benzyl acrylate, benzyl methacrylate, 2-n-butoxyethyl acrylate, 2-n-butoxyethyl methacrylate, 2-chloroethyl acrylate, 2-chloroethyl methacrylate, sec-butyl acrylate, sec-butyl methacrylate, tert-butyl acrylate, tert-butyl methacrylate, 2-ethylbutyl acrylate, 2-ethylbutyl methacrylate, cinnamyl acrylate, cinnamyl methacrylate, cyclohexyl acrylate, cyclohexyl methacrylate, cyclopentyl acrylate, cyclopentyl methacrylate, 2-ethoxyethyl acrylate, 2-ethoxyethyl methacrylate, furfuryl acrylate, furfuryl methacrylate, hexafluoroisopropyl acrylate, hexafluoroisopropyl methacrylate, 3-methoxybutyl acrylate, 3-methoxybutyl methacrylate, 2-methoxybutyl acrylate, 2-methoxybutyl methacrylate, 2-nitro-2-methylpropyl acrylate, 2-nitro-2-methylpropyl methacrylate, n-octyl-acrylate, n-octyl-methacrylate, 2-ethylhexyl acrylate, 2-ethylhexyl methacrylate, 2-phenoxyethyl acrylate, 2-phenoxyethyl methacrylate, 2-phenylethyl acrylate, 2-phenylethyl methacrylate, phenyl acrylate, phenyl methacrylate, propargyl acrylate, propargyl methacrylate, tetrahydrofurfuryl acrylate, tetrahydrofurfuryl methacrylate, tetrahydropyranyl acrylate, tetrahydropyranyl methacrylate, styrene, and α-methylstyrene, or combination of any two or more thereof.

The polymerization composition may include from about 1 wt % to about 99 wt % of the at least one acrylic monomer, based upon the total weight of monomers in the composition. This includes from about 3 wt % to about 90 wt %, from about 10 wt % to about 80 wt %, from about 20 wt % to about 70 wt %, from about 30 wt % to about 60 wt %, or from about 40 wt % to about 50 wt %, of the at least one acrylic monomer, based upon the total weight of monomers in the composition, and ranges between any two of these values or less than any one of these values. The polymerization composition may include from about 1 wt % to about 99 wt % of the at least one methacrylic monomer, based upon the total weight of monomers in the composition. This includes from about 3 wt % to about 90 wt %, from about 10 wt % to about 80 wt %, from about 20 wt % to about 70 wt %, from about 30 wt % to about 60 wt %, or from about 40 wt % to about 50 wt %, of the at least one methacrylic monomer, based upon the total weight of monomers in the composition, and ranges between any two of these values or less than any one of these values. The polymerization composition may include from 0 wt % to about 30 wt % of a styrenic monomer, based upon the total weight of monomers in the composition. This includes from about 0 wt % to about 20 wt %, from about 0 wt % to about 10 wt %, from about 5 wt % to about 15 wt %, or from about 5 wt % to about 10 wt %, of the at least one methacrylic monomer, based upon the total weight of monomers in the composition, and ranges between any two of these values or less than any one of these values.

The photoinitiator used in the methods is described herein and includes a benzophenone moiety, a nitrogen-containing moiety covalently bonded to the benzophenone moiety, and an unsaturated polymerizable moiety covalently bonded to the nitrogen-containing moiety. The polymerizable mixture may include from about 1 wt % to about 70 wt % of the photoinitiator, based upon the total weight of monomers in the mixture. This includes from about 3 wt % to about 60 wt %, from about 5 wt % to about 50 wt %, from about 10 wt % to about 40 wt %, or from about 20 wt % to about 30 wt %, of the photoinitiator, based upon the total weight of the polymerizable mixture, and ranges between any two of these values or less than any one of these values.

The polymerizable mixture may further include suitable additives depending upon the desired end use. Exemplary additives include solvents, diluents, initiators, catalysts, resins, binders, plasticizers, pigments, dyes, fillers, pigments, dyes, antioxidants, thixotropic agents, indicators, stabilizers, inhibitors, UV absorbers, and the like. The additives, if present, may be incorporated for example, at a concentration in the range of about 0.001 wt %, about 0.01 wt %, about 0.02 wt %, about 0.05 wt %, about 0.1 wt %, about 0.5 wt %, about 1.0 wt %, about 2 wt %, about 5 wt %, about 10.0 wt %, about 15.0 wt %, about 20.0 wt %, about 30.0 wt %, based upon the total weight of the polymerizable mixture, and ranges between any two of these values or less than any one of these values.

The polymerizable mixture is illuminated with light from a light source. The mixture may be illuminated using a variety of light sources. For example the mixture may be illuminated using light sources that emit ultraviolet (UV) or visible light such as quartz halogen lamps, tungsten-halogen lamps, mercury lamps, xenon and mercury/xenon lamps, plasma arcs, light emitting diodes, and lasers, or a combination of any two or more thereof. Devices that do not depend on light emission, e.g., electron beam (EB) irradiation may also be used to illuminate the compositions. In some embodiments, a combination of light emitting methods and non-light emitting methods, e.g., UV-EB, may be used.

In some embodiments, the light source is a source of visible light. In other embodiments, the light source is a source of ultraviolet light. In some embodiments, the light source is a light emitting diode, a mercury lamp, a laser, or a combination of any two or more thereof. In some embodiments, the light source is a light emitting diode.

In one aspect, a method for polymerizing unsaturated polymerizable composition to provide a photocurable composition is provided. The method includes mixing a photoinitiator with a polymerization mixture to form polymerizable composition and subjecting the composition to polymerization. In one embodiment, the polymerizable composition includes an acrylate, a methacrylate, or a styrenic monomer. In one embodiment, the photoinitiator includes a benzophenone moiety, a nitrogen-containing moiety covalently bonded to the benzophenone moiety, and an unsaturated polymerizable moiety covalently bonded to the nitrogen-containing moiety. In some embodiments, the polymerization may include photopolymerization. In some embodiments, the polymerization may include illuminating the polymerizable composition with light from a light source.

In one aspect, a method of curing a photocurable coating is provided, wherein the method includes illuminating the photocurable coating with light from a light emitting diode. The photocurable coating includes an acrylate, a methacrylate, or a styrenic monomer and a photoinitiator. Suitable acrylate, methacrylate, and styrenic monomers are described herein. The photoinitiator used in the curing method is described herein and includes a benzophenone moiety, a nitrogen-containing moiety covalently bonded to the benzophenone moiety, and an unsaturated polymerizable moiety covalently bonded to the nitrogen-containing moiety. Suitable light sources are described herein and include visible light, ultraviolet light, light emitting diode, a mercury lamp, a laser, or a combination of any two or more thereof.

In some embodiments, heat or an inert atmosphere is used to accelerate the curing process. In the process, the temperature and time used may be sufficient to effect polymerization. For example, the temperature may be 130° C. or greater. This includes, in some embodiments, the temperature being from about 130° C. to about 240° C., inclusive. In other embodiments, the temperature is about 150° C. to about 160° C. In further embodiments, the temperature is about 160° C. to about 200° C. In further embodiments, the curing is conducted at room temperature. With regard to the time of the curing, it may be from about 2 seconds to about 120 minutes. In some embodiments, this includes from about 10 seconds to about 90 min, from about 30 seconds to about 60 min, from about 1 min to about 45 min, from about 10 min to about 30 min, or from about 15 min to about 20 min, and ranges between any two of these values or less than any one of these values.

In some embodiments, the method further includes applying the photocurable coating to a substrate. The photocurable substrate may be applied to the substrate before or after curing. The photocurable coating may be applied onto a variety of substrates, including, for example, metal, paper, packaging materials, cloth, paperboard, foils, glass, fiber glass, plastics, dental inserts, rubber, cellophane, and wood, and the like or any other substrate which can adhere to the coating. In some embodiments, the substrate includes paper. In some embodiments, the substrate includes metal sheets. In some embodiments, the substrate includes plastic films and sheets, such as those derived from polyethylene terephthalate, polystyrene, rubber hydrochloride, polyvinyl chloride, and polyvinylidene chloride or the like. Depending on the substrate, the end-use and the coating conditions, the method may including adding additives to the photocurable coating. Suitable additives include, but are not limited to, adhesives, solvents, fillers, binders, inhibitors, dispersants, pigments, dyes, resins, thixotropic agents, drying agents, stabilization agent, plasticizer, other photoinitiators, and the like or a combination of two or more thereof. In some embodiments, the substrate is paper. In other embodiments, the substrate is plastic. In some embodiments, the substrate is packaging material, e.g., laminate substrates, vinyl, plastic film or foils, metal film or foils, and paper. In some embodiments, the substrate includes paper, an aluminum foil, a polyester film, or a polypropylene film.

In one aspect, a photocurable composition is provided. The composition includes an acrylate, a methacrylate, or a styrenic monomer and a photoinitiator.

Suitable acrylate, methacrylate, and styrenic monomers are described herein. The photoinitiator is as described herein and includes a benzophenone moiety, a nitrogen-containing moiety covalently bonded to the benzophenone moiety, and an unsaturated polymerizable moiety covalently bonded to the nitrogen-containing moiety.

In addition to the monomers and photoinitiators described above, the photocurable composition may include other additives such as adhesives, solvents, fillers, binders, inhibitors, dispersants, pigments, dyes, resins, thixotropic agents, drying agents, stabilization agent, plasticizer, other photoinitiators, adhesion promoters, waxes, conductive materials, antistatic agents, surface active agents, antimicrobials and materials intended to affect permeability to moisture, oxygen, or other migratory liquids, gases, or vapors. In some embodiments, the photocurable composition further includes at least one of a pigment, a resin, a stabilization agent, a plasticizer, or an additional photoinitiator.

The photocurable compositions have a number of applications. These applications include, but are not limited to, binders for use for UV/EB cure markets, hot-melt/pressure sensitive adhesives, in-mold coatings, and low cure temperature powder coatings. In some embodiments, the compositions described herein may be used as coatings or coating compositions, such as for example, a clear coating or a pigmented coating such as an ink or paint. In some embodiments, the coatings or coating compositions are inks, or ink compositions. In some embodiments, the photocurable compositions may be used in UV and EB curable ink and coating compositions. The photocurable composition make also be used in additive manufacturing processes such as stereolithography, for optical fibre coatings, and for automotive applications. In some embodiments, the photocurable composition is a coating composition, a packaging composition, or an ink composition. In some embodiments, the photocurable composition is a curable ink for packaging printing applications. In some embodiments, the photocurable composition is a curable ink for food packaging applications.

Various aspects of the invention are set out in the following paragraphs.

Para. A. A photoinitiator including a benzophenone moiety, a nitrogen-containing moiety covalently bonded to the benzophenone moiety, and an unsaturated polymerizable moiety covalently bonded to the nitrogen-containing moiety Para. B. The photoinitiator of Para. A, wherein the unsaturated polymerizable moiety includes an acrylate group or a methacrylate group.

Para. C. The photoinitiator of Para. A or B, wherein the nitrogen-containing moiety is an azetidinyl, pyrrolidinyl, piperazinyl, piperidinyl, azepanyl, azocanyl, or a group of formula —RNR'H, where R is an alkylenyl group joining the nitrogen atom to the benzophenone, and R' is an alkyl group.

Para. D. The photoinitiator of any one of Paras. A-C, wherein the nitrogen-containing moiety is a piperazinyl based moiety.

Para. E. The photoinitiator of any one of Paras. A-D, which is represented by the following formula (I):

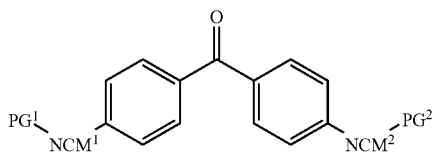

(I)

wherein:
NCM1 is a first nitrogen-containing moiety where the nitrogen is covalently bonded to a first phenyl group of the benzophenone;
NCM2 is a bond, H, or a second nitrogen-containing moiety where the nitrogen is covalently bonded to a second phenyl group of the benzophenone;
PG1 is an acrylate-containing group or a methacrylate-containing group; and
PG2 is absent, H, an acrylate-containing group or a methacrylate-containing group.

Para. F. The photoinitiator of Para. E, wherein $PG^1$ and $PG^2$ are an acrylate-containing group or a methacrylate-containing group.

Para. G. The photoinitiator of any one of Paras. E-F, wherein the at least one of $NCM^1$ and $NCM^2$ is an azetidinyl, pyrrolidinyl, piperazinyl, piperidinyl, azepanyl, azocanyl, or a group of formula —RNR'H, where R is an alkylenyl group joining the nitrogen atom to the benzophenone, and R' is an alkyl group.

Para. H. The photoinitiator of any one of Paras. E-G, wherein the at least one of $NCM^1$ and $NCM^2$ is a piperazine-based moiety.

Para. I. The photoinitiator of any one of Paras. A-H, which is represented by the formula (II):

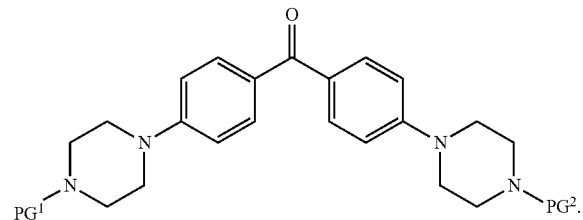

(II)

Para. J. The photoinitiator of Para. I, wherein $PG^1$ and $PG^2$ are an acrylate-containing group or a methacrylate-containing group.

Para. K. The photoinitiator of any one of Paras. E-J, wherein $PG^1$ and $PG^2$ are individually an acrylate-containing group having two or more acrylate moieties, or a methacrylate-containing group having two or more methacrylate moieties.

Para. L. The photoinitiator of any one of Paras. E-K, wherein $PG^1$ and $PG^2$ are selected from the group consisting of:

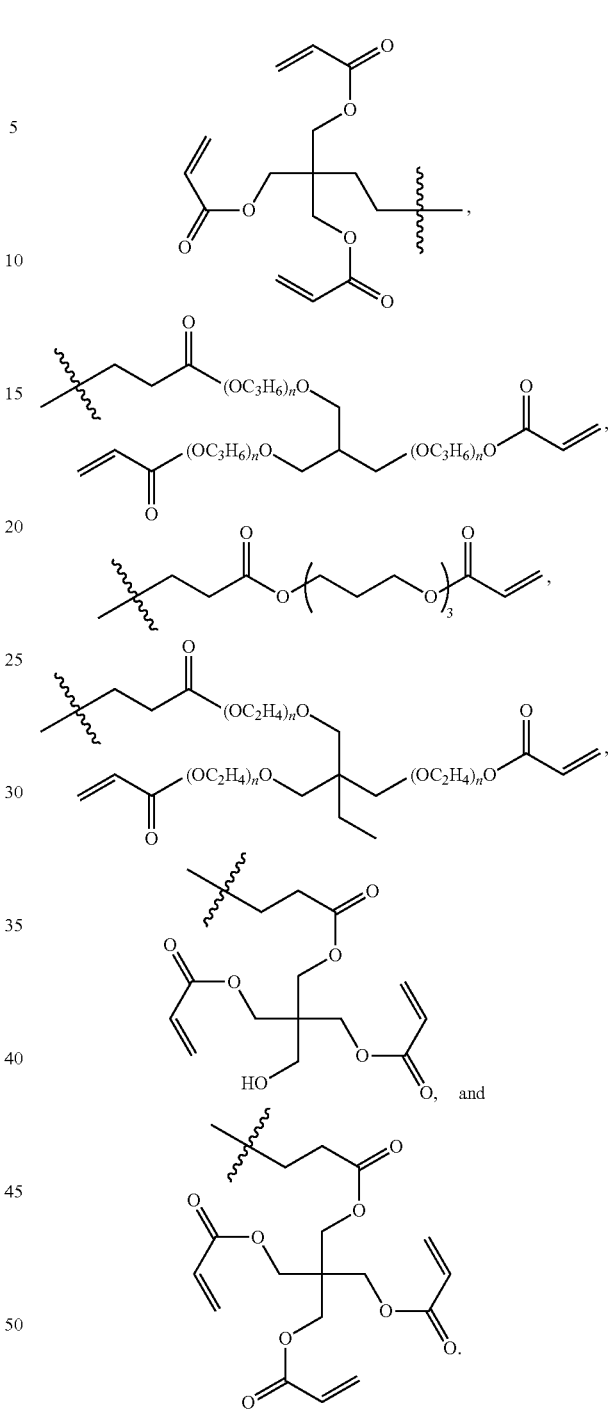

Para. M. A method of polymerization, the method including mixing a photoinitiator with a polymerization composition to form a polymerizable mixture; and illuminating the polymerizable mixture with light from a light source; wherein: the polymerization composition includes an acrylate, a methacrylate, or a styrenic monomer; and the photoinitiator includes: a benzophenone moiety; a nitrogen-containing moiety covalently bonded to the benzophenone moiety; and an unsaturated polymerizable moiety covalently bonded to the nitrogen-containing moiety.

Para. N. The method of Para. M, wherein the light source is a source of visible light or ultraviolet light.

Para. O. The method of Para. M, wherein the light source is a light emitting diode, a mercury lamp, a laser, or combination of any two or more thereof.

Para. P. A method of curing a photocurable coating composition, the method including illuminating the photocurable coating composition with light from a light emitting diode; wherein the photocurable coating composition includes an acrylate, a methacrylate, or a styrenic monomer; and a photoinitiator; and the photoinitiator includes a benzophenone moiety, a nitrogen-containing moiety covalently bonded to the benzophenone moiety, and an unsaturated polymerizable moiety covalently bonded to the nitrogen-containing moiety.

Para. Q. The method of any one of Paras. M-P, wherein the acrylic, methacrylic, or styrenic monomer includes acrylic acid, methacrylic acid, methyl methacrylate, ethyl acrylate, ethyl methacrylate, n-propyl acrylate, n-propyl methacrylate, n-butyl acrylate, n-butyl methacrylate, isopropyl acrylate, isopropyl methacrylate, isobutyl acrylate, isobutyl methacrylate, n-amyl acrylate, n-amyl methacrylate, n-hexyl acrylate, n-hexyl methacrylate, isoamyl acrylate, isoamyl methacrylate, trifluoroethyl acrylate, trifluoroethyl methacrylate, benzyl acrylate, benzyl methacrylate, 2-n-butoxyethyl acrylate, 2-n-butoxyethyl methacrylate, 2-chloroethyl acrylate, 2-chloroethyl methacrylate, sec-butyl acrylate, sec-butyl methacrylate, tert-butyl acrylate, tert-butyl methacrylate, 2-ethylbutyl acrylate, 2-ethylbutyl methacrylate, cinnamyl acrylate, cinnamyl methacrylate, cyclohexyl acrylate, cyclohexyl methacrylate, cyclopentyl acrylate, cyclopentyl methacrylate, 2-ethoxyethyl acrylate, 2-ethoxyethyl methacrylate, furfuryl acrylate, furfuryl methacrylate, hexafluoroisopropyl acrylate, hexafluoroisopropyl methacrylate, 3-methoxybutyl acrylate, 3-methoxybutyl methacrylate, 2-methoxybutyl acrylate, 2-methoxybutyl methacrylate, 2-nitro-2-methylpropyl acrylate, 2-nitro-2-methylpropyl methacrylate, n-octyl-acrylate, n-octyl-methacrylate, 2-ethylhexyl acrylate, 2-ethylhexyl methacrylate, 2-phenoxyethyl acrylate, 2-phenoxyethyl methacrylate, 2-phenylethyl acrylate, 2-phenylethyl methacrylate, phenyl acrylate, phenyl methacrylate, propargyl acrylate, propargyl methacrylate, tetrahydrofurfuryl acrylate, tetrahydrofurfuryl methacrylate, tetrahydropyranyl acrylate, tetrahydropyranyl methacrylate, styrene, or α-methylstyrene.

Para. R. The method of any one of Paras. M-Q, wherein the unsaturated polymerizable moiety includes an acrylate group or a methacrylate group.

Para. S. The method of any one of Paras. M-R, wherein the nitrogen-containing moiety is an azetidinyl, pyrrolidinyl, piperazinyl, piperidinyl, azepanyl, azocanyl, or a group of formula —RNR'H, where R is an alkylenyl group joining the nitrogen atom to the benzophenone, and R' is an alkyl group.

Para. T. The method of any one of Paras. M-S, wherein the nitrogen-containing moiety is a piperazinyl based moiety.

Para. U. The method of any one of Paras. M-T, wherein the photoinitiator is represented by the following formula (I):

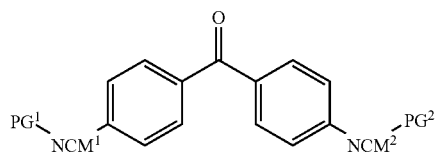

wherein:
NCM$^1$ is a first nitrogen-containing moiety where the nitrogen is covalently bonded to a first phenyl group of the benzophenone;
NCM$^2$ is a bond, H, or a second nitrogen-containing moiety where the nitrogen is covalently bonded to a second phenyl group of the benzophenone;
PG$^1$ is an acrylate-containing group or a methacrylate-containing group; and
PG$^2$ is absent, H, an acrylate-containing group or a methacrylate-containing group.

Para. V. The method of Para. U, wherein PG$^1$ and PG$^2$ are an acrylate-containing group or a methacrylate-containing group.

Para. W. The method of any one of Paras. U-V, wherein the at least one of NCM$^1$ and NCM$^2$ is an azetidinyl, pyrrolidinyl, piperazinyl, piperidinyl, azepanyl, azocanyl, or a group of formula —RNR'H, where R is an alkylenyl group joining the nitrogen atom to the benzophenone, and R' is an alkyl group.

Para. X. The method of any one of Paras. U-W, wherein the at least one of NCM$^1$ and NCM$^2$ is a piperazine-based moiety.

Para. Y. The method of any one of Paras. M-X, wherein the photoinitiator is represented by the formula (II):

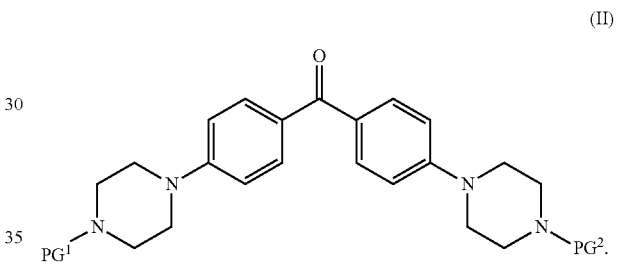

Para. Z. The method of Para. Y, wherein PG$^1$ and PG$^2$ are an acrylate-containing group or a methacrylate-containing group.

Para. AA. The method of any one of Paras. M-Z, wherein PG$^1$ and PG$^2$ are individually an acrylate-containing group having two or more acrylate moieties, or a methacrylate-containing group having two or more methacrylate moieties.

Para. BB. The method of any one of Paras. M-AA, wherein PG$^1$ and PG$^2$ are selected from the group consisting of:

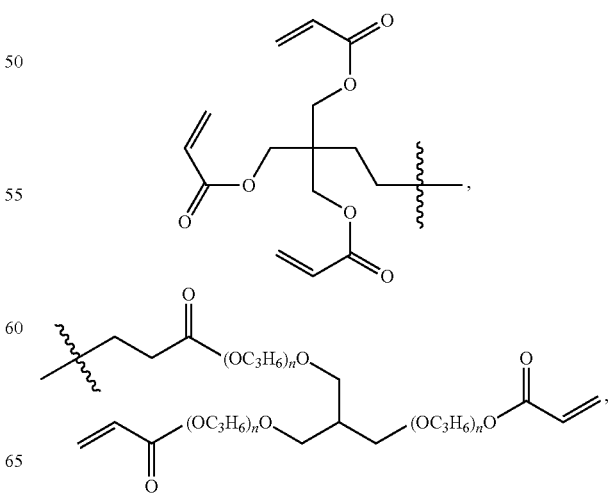

-continued

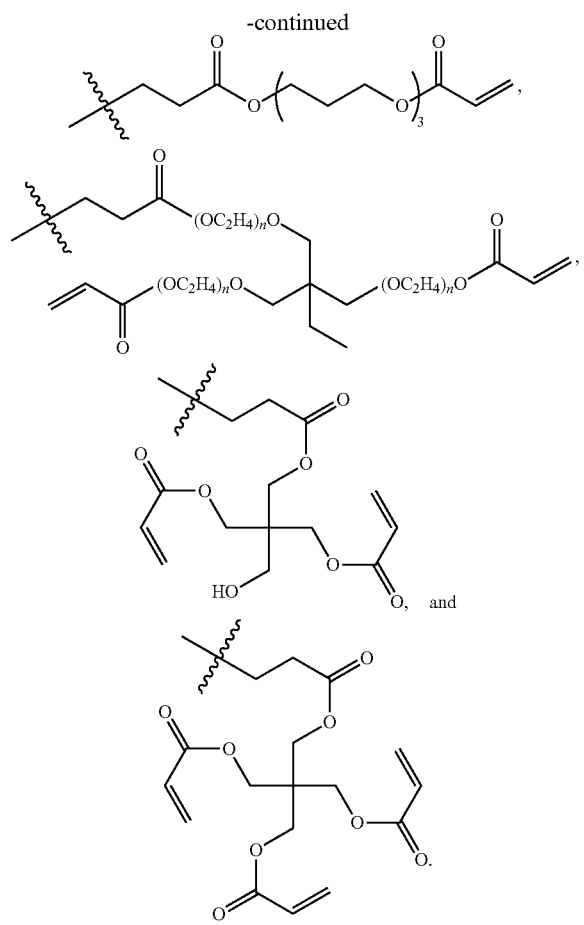

Para. CC. The method of any one of Paras. P-BB, further including applying the photocurable coating to a substrate prior to curing.

Para. DD. The method of Para. CC, wherein the substrate includes paper, an aluminum foil, a polyester film, or a polypropylene film.

Para. EE. A photocurable composition which includes an acrylate, a methacrylate, or a styrenic monomer; and a photoinitiator; wherein the photoinitiator comprises a benzophenone moiety, a nitrogen-containing moiety covalently bonded to the benzophenone moiety, and an unsaturated polymerizable moiety covalently bonded to the nitrogen-containing moiety.

Para. FF. The photocurable composition of Para. EE, wherein the acrylic, methacrylic, or styrenic monomer includes acrylic acid, methacrylic acid, methyl methacrylate, ethyl acrylate, ethyl methacrylate, n-propyl acrylate, n-propyl methacrylate, n-butyl acrylate, n-butyl methacrylate, isopropyl acrylate, isopropyl methacrylate, isobutyl acrylate, isobutyl methacrylate, n-amyl acrylate, n-amyl methacrylate, n-hexyl acrylate, n-hexyl methacrylate, isoamyl acrylate, isoamyl methacrylate, trifluoroethyl acrylate, trifluoroethyl methacrylate, benzyl acrylate, benzyl methacrylate, 2-n-butoxyethyl acrylate, 2-n-butoxyethyl methacrylate, 2-chloroethyl acrylate, 2-chloroethyl methacrylate, sec-butyl acrylate, sec-butyl methacrylate, tert-butyl acrylate, tert-butyl methacrylate, 2-ethylbutyl acrylate, 2-ethylbutyl methacrylate, cinnamyl acrylate, cinnamyl methacrylate, cyclohexyl acrylate, cyclohexyl methacrylate, cyclopentyl acrylate, cyclopentyl methacrylate, 2-ethoxyethyl acrylate, 2-ethoxyethyl methacrylate, furfuryl acrylate, furfuryl methacrylate, hexafluoroisopropyl acrylate, hexafluoroisopropyl methacrylate, 3-methoxybutyl acrylate, 3-methoxybutyl methacrylate, 2-methoxybutyl acrylate, 2-methoxybutyl methacrylate, 2-nitro-2-methylpropyl acrylate, 2-nitro-2-methylpropyl methacrylate, n-octyl-acrylate, n-octyl-methacrylate, 2-ethylhexyl acrylate, 2-ethylhexyl methacrylate, 2-phenoxyethyl acrylate, 2-phenoxyethyl methacrylate, 2-phenylethyl acrylate, 2-phenylethyl methacrylate, phenyl acrylate, phenyl methacrylate, propargyl acrylate, propargyl methacrylate, tetrahydrofurfuryl acrylate, tetrahydrofurfuryl methacrylate, tetrahydropyranyl acrylate, tetrahydropyranyl methacrylate, styrene, or α-methylstyrene.

Para. GG. The photocurable composition of any one of Paras. EE-FF, wherein the unsaturated polymerizable moiety includes an acrylate group or a methacrylate group.

Para. HH. The photocurable composition of any one of Paras. EE-GG, wherein the nitrogen-containing moiety is an azetidinyl, pyrrolidinyl, piperazinyl, piperidinyl, azepanyl, azocanyl, or a group of formula —RNR'H, where R is an alkylenyl group joining the nitrogen atom to the benzophenone, and R' is an alkyl group.

Para. II. The photocurable composition of any one of Paras. EE-HH, wherein the nitrogen-containing moiety is a piperazinyl based moiety.

Para. JJ. The photocurable composition of any one of Paras. EE-II, wherein the photoinitiator is represented by the following formula (I):

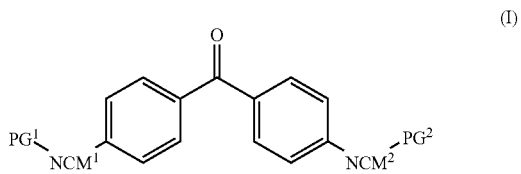

(I)

wherein:
$NCM^1$ is a first nitrogen-containing moiety where the nitrogen is covalently bonded to a first phenyl group of the benzophenone;
$NCM^2$ is a bond, H, or a second nitrogen-containing moiety where the nitrogen is covalently bonded to a second phenyl group of the benzophenone;
$PG^1$ is an acrylate-containing group or a methacrylate-containing group; and
$PG^2$ is absent, H, an acrylate-containing group or a methacrylate-containing group.

Para. KK. The photocurable composition of Para. JJ, wherein $PG^1$ and $PG^2$ are an acrylate-containing group or a methacrylate-containing group.

Para. LL. The photocurable composition of any one of Paras. JJ-KK, wherein the at least one of $NCM^1$ and $NCM^2$ is an azetidinyl, pyrrolidinyl, piperazinyl, piperidinyl, azepanyl, azocanyl, or a group of formula —RNR'H, where R is an alkylenyl group joining the nitrogen atom to the benzophenone, and R' is an alkyl group.

Para. MM. The photocurable composition of any one of Paras. JJ-LL, wherein the at least one of $NCM^1$ and $NCM^2$ is a piperazine-based moiety.

Para. NN. The photocurable composition of any one of Paras. EE-MM, wherein the photoinitiator is represented by the formula (II):

(II)

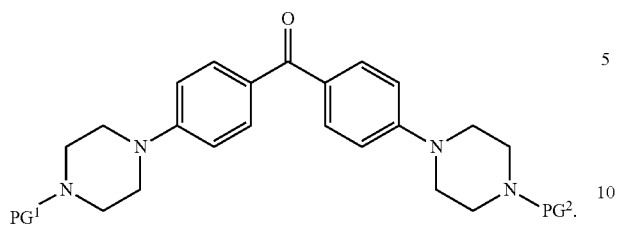

Para. OO. The photocurable composition of Para. NN, wherein PG¹ and PG² are an acrylate-containing group or a methacrylate-containing group.

Para. PP. The photocurable composition of any one of Paras. JJ-OO, wherein PG¹ and PG² are individually an acrylate-containing group having two or more acrylate moieties, or a methacrylate-containing group having two or more methacrylate moieties.

Para. QQ. The photocurable composition of any one of Paras. JJ-PP, wherein PG¹ and PG² are selected from the group consisting of:

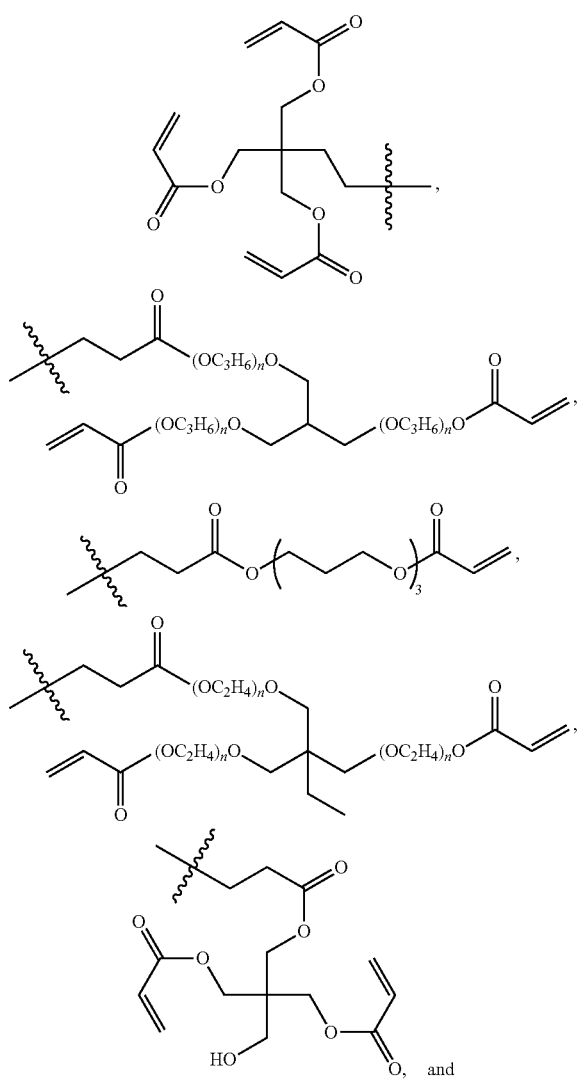

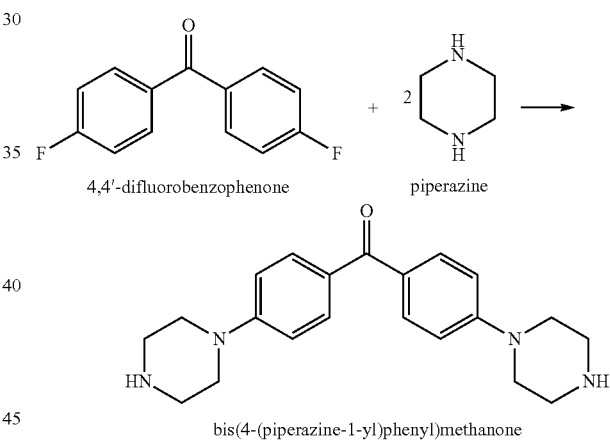

The present invention, thus generally described, will be understood more readily by reference to the following examples, which are provided by way of illustration and are not intended to be limiting of the present invention.

EXAMPLES

Example 1

Synthesis of a low-migration photoinitiator. Step 1: synthesis of bis-(4-(piperazin-1-yl)phenyl)methanone ("MK(pipaz)$_2$", where "MK" is an abbreviation for Michler's Ketone)"

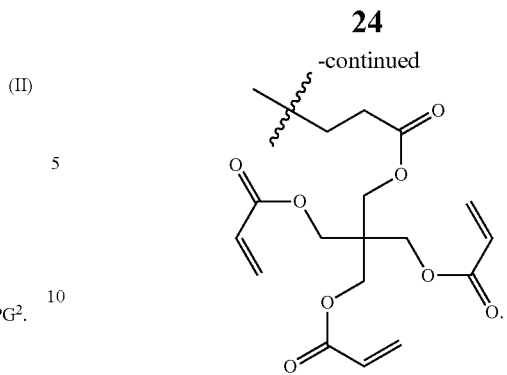

4,4'-difluorobenzophenone    piperazine bis(4-(piperazine-1-yl)phenyl)methanone

Each step of the process is conducted in a room equipped with UV-filtered lighting. Piperazine (344.60 g, 4.00 mol), 4,4'-difluorobenzophenone (DFBP) (87.30 g, 0.400 mol), dimethyl sulfoxides (DMSO; 500 g) were added to a 1 L reaction flask to form an opaque, white slurry, with stirring using a Teflon stirring blade and rod. Using an open system with an uncooled condenser (to minimize piperazine condensation), the slurry is heated at 145° C. for a total of 40 h, over several days.

At 40 h, the heat is removed and the reaction mixture is poured hot into a beaker with 2000 g ice, which is itself housed in an ice bath. The flask was then washed with deionized water (100 g) and DMSO (100 g). A cloudy slurry was formed. The slurry was then filtered on a Büchner funnel to collect a waxy solid. The solid was collected and dried overnight to yield 192 g of crude MK(pipaz)$_2$. The crude MK(pipaz)$_2$ was heated in ethanol (1750 g) to form opaque slurry, which was filtered vacuum filtration.

The ethanol filtrate was collected and the solvent removed to yield MK(pipaz)$_2$ (93.17 g, 66.02% yield).

Step 2: Synthesis of an Acrylate Functional Photoinitiator:

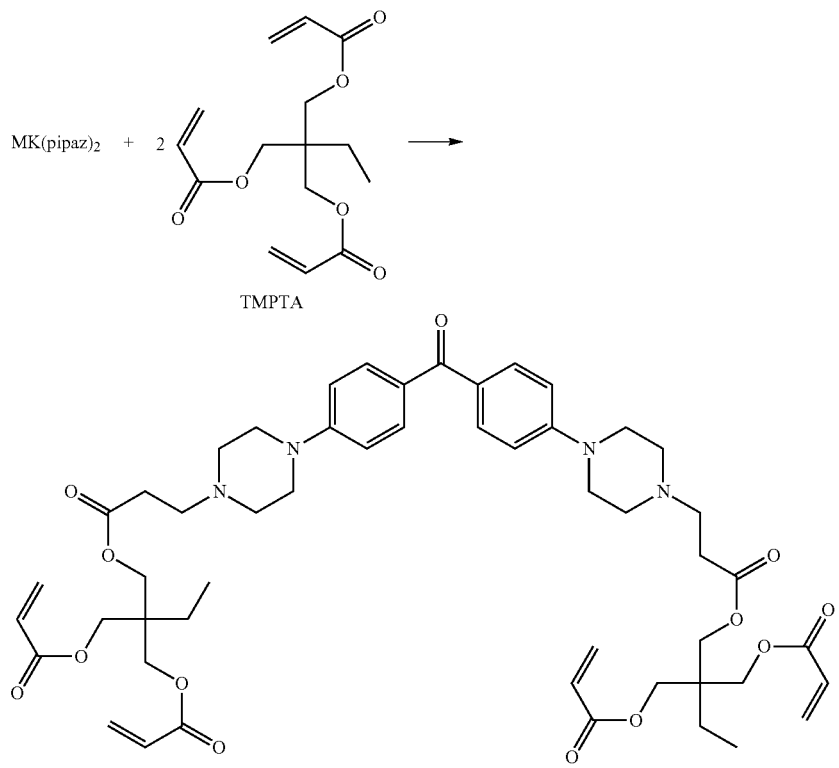

MK(pipaz)$_2$ (5.00 g) was added to trimethylolpropane triacrylate (TMPTA, 8.75) in a flask with ethanol (5.00 g) and the mixture was heated on a hot plate until the MK(pipaz)$_2$ dissolved, with stirring. The mixture was heated at 100° C. for 1 h to evaporate the ethanol from the mixture to provide a viscous, tacky yellow material.

Example 2

Curing of the acrylate functional photoinitiator from Example 1. A drop of the acrylate functional photoinitiator from Example 1 was put onto a microscope slide and drawn into a film with the flat end of another glass slide to form a smear. The smear was placed under a Phoseon RX10 LED-curing lamp with about ½ inch of clearance from the surface to the lamp. The computer settings for the curing conditions were: 6.5 Amps; UV on time=90%; pulses=30 Hz; and cure time=60 sec. The material had cured onto the microscope slide as a yellow-flexible film that could be peeled off the glass surface with a little force from a metal spatula.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A photoinitiator represented by Formula (I):

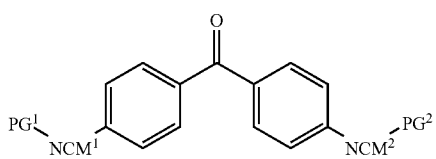

wherein:
NCM$^1$ is a first nitrogen-containing moiety where the nitrogen is covalently bonded to a first phenyl group of the benzophenone;
NCM$^2$ is a bond, H, or a second nitrogen-containing moiety where the nitrogen is covalently bonded to a second phenyl group of the benzophenone;
wherein PG$^1$ and PG$^2$ are independently selected from the group consisting of:

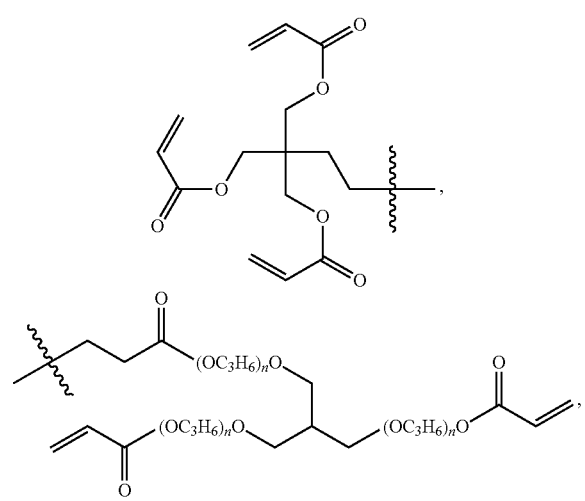

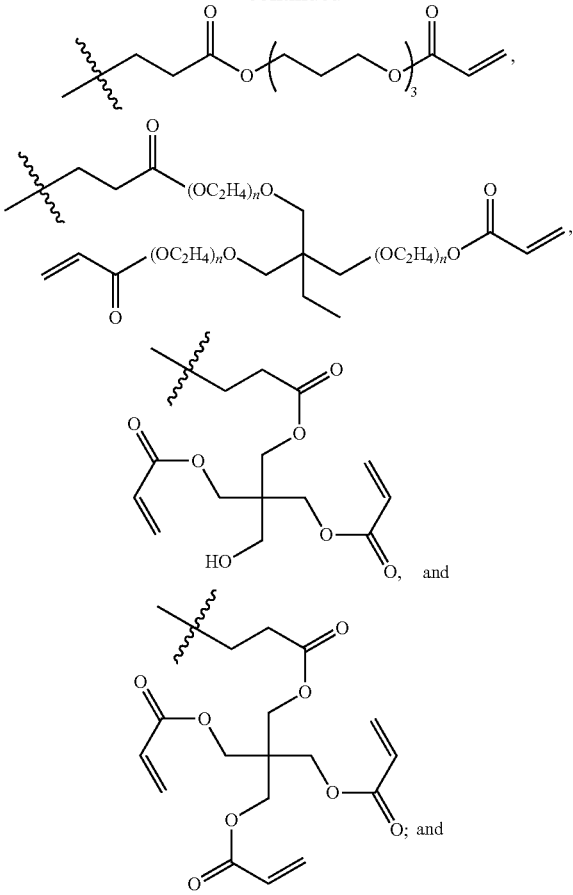

wherein n is an integer.

2. The photoinitiator of claim 1, wherein at least one of NCM$^1$ and NCM$^2$ is an azetidinyl, pyrrolidinyl, piperazinyl, piperidinyl, azepanyl, azocanyl, or a group of formula —RNR'H, where R is an alkylenyl group joining the nitrogen atom to the benzophenone, and R' is an alkyl group.

3. The photoinitiator of claim 1, wherein at least one of NCM$^1$ and NCM$^2$ is a piperazine-based moiety.

4. The photoinitiator of claim 1, which is represented by Formula (II):

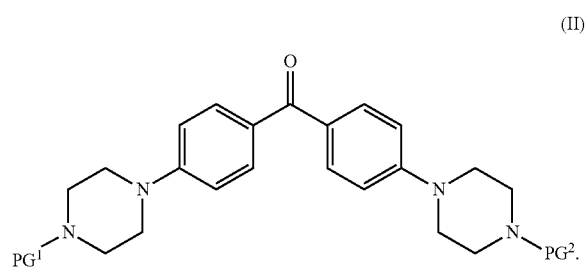

5. A photocurable composition comprising:
an acrylate, a methacrylate, or a styrenic monomer; and
the photoinitiator of claim 1.

6. A photocurable composition comprising:
an acrylate, a methacrylate, or a styrenic monomer; and
the photoinitiator of claim 2.

7. A photocurable composition comprising:
an acrylate, a methacrylate, or a styrenic monomer; and
the photoinitiator of claim 3.

8. A photocurable composition comprising:
an acrylate, a methacrylate, or a styrenic monomer; and
the photoinitiator of claim 4.

9. The photocurable composition of claim 5, wherein the acrylic, methacrylic, or styrenic monomer comprises acrylic acid, methacrylic acid, methyl methacrylate, ethyl acrylate, ethyl methacrylate, n-propyl acrylate, n-propyl methacrylate, n-butyl acrylate, n-butyl methacrylate, isopropyl acrylate, isopropyl methacrylate, isobutyl acrylate, isobutyl methacrylate, n-amyl acrylate, n-amyl methacrylate, n-hexyl acrylate, n-hexyl methacrylate, isoamyl acrylate, isoamyl methacrylate, trifluoroethyl acrylate, trifluoroethyl methacrylate, benzyl acrylate, benzyl methacrylate, 2-n-butoxyethyl acrylate, 2-n-butoxyethyl methacrylate, 2-chloroethyl acrylate, 2-chloroethyl methacrylate, sec-butyl acrylate, sec-butyl methacrylate, tert-butyl acrylate, tert-butyl methacrylate, 2-ethylbutyl acrylate, 2-ethylbutyl methacrylate, cinnamyl acrylate, cinnamyl methacrylate, cyclohexyl acrylate, cyclohexyl methacrylate, cyclopentyl acrylate, cyclopentyl methacrylate, 2-ethoxyethyl acrylate, 2-ethoxyethyl methacrylate, furfuryl acrylate, furfuryl methacrylate, hexafluoroisopropyl acrylate, hexafluoroisopropyl methacrylate, 3-methoxybutyl acrylate, 3-methoxybutyl methacrylate, 2-methoxybutyl acrylate, 2-methoxybutyl methacrylate, 2-nitro-2-methylpropyl acrylate, 2-nitro-2-methylpropyl methacrylate, n-octyl-acrylate, n-octyl-methacrylate, 2-ethylhexyl acrylate, 2-ethylhexyl methacrylate, 2-phenoxyethyl acrylate, 2-phenoxyethyl methacrylate, 2-phenylethyl acrylate, 2-phenylethyl methacrylate, phenyl acrylate, phenyl methacrylate, propargyl acrylate, propargyl methacrylate, tetrahydrofurfuryl acrylate, tetrahydrofurfuryl methacrylate, tetrahydropyranyl acrylate, tetrahydropyranyl methacrylate, styrene, or α-methylstyrene.

10. The photocurable composition of claim 5 further comprising at least one of a pigment, a resin, a stabilization agent, a plasticizer, or an additional photoinitiator.

11. The photocurable composition of claim 5 which is a coating composition, a packaging composition, or an ink composition.

12. A compound represented by Formula (II):

(II)

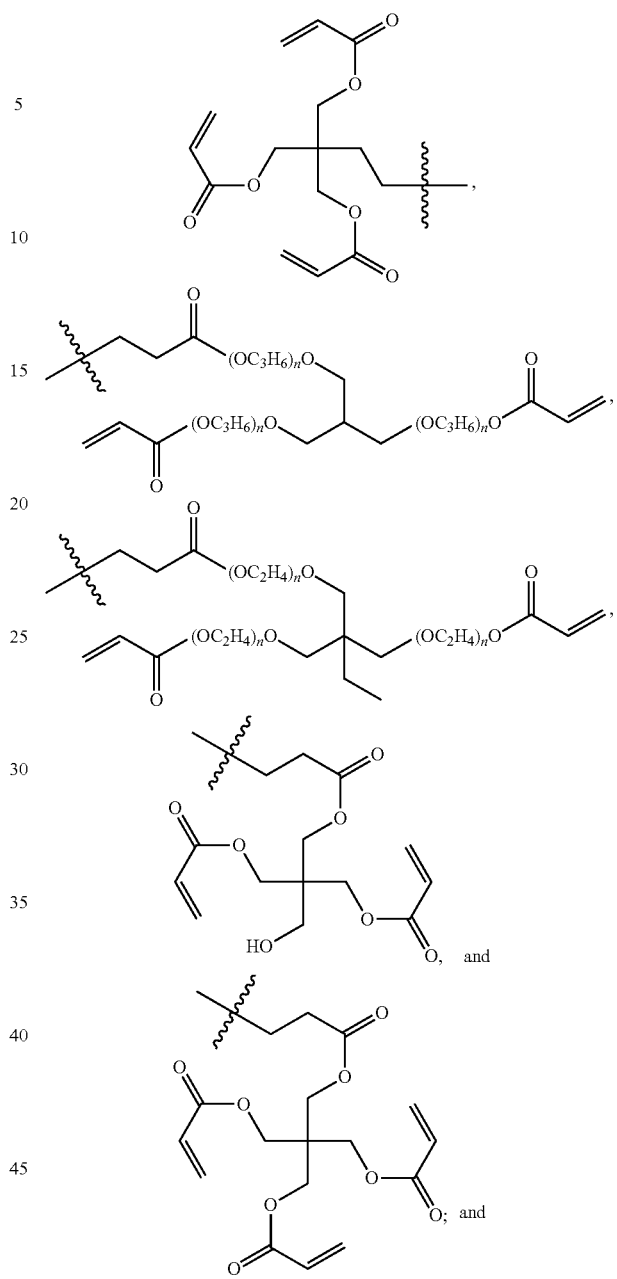

wherein: $PG^1$ and $PG^2$ are selected from the group consisting of:

wherein n is an integer.

13. The compound of claim 12, wherein $PG^1$ and $PG^2$ are:

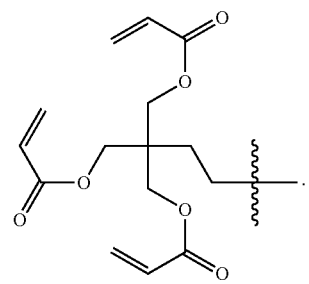 [SMILES: *CCC(COC(=O)C=C)(COC(=O)C=C)COC(=O)C=C]

14. A polymer comprising a monomeric unit comprising the compound of claim 12.

15. The photoinitiator of claim 1, wherein n is an integer up to 15.

16. The photoinitiator of claim 15, wherein n is 1, 2, or 3.

17. The photoinitiator of claim 12, wherein n is an integer up to 15.

18. The photoinitiator of claim 17, wherein n is 1, 2, or 3.

* * * * *